United States Patent [19]

Malem

[11] 4,452,239

[45] Jun. 5, 1984

[54] MEDICAL NEBULIZING APPARATUS

[76] Inventor: Hilal Malem, 4 Rufford Rd., Sherwood, Nottingham NG5 2NR, England

[21] Appl. No.: 321,164

[22] PCT Filed: Mar. 24, 1981

[86] PCT No.: PCT/GB81/00055

§ 371 Date: Nov. 9, 1981

§ 102(e) Date: Nov. 9, 1981

[87] PCT Pub. No.: WO81/02676

PCT Pub. Date: Oct. 1, 1981

[30] Foreign Application Priority Data
Mar. 25, 1980 [GB] United Kingdom ................. 8010010
[51] Int. Cl.3 ............................................. A61M 15/00
[52] U.S. Cl. .......................... 128/200.17; 128/200.14; 128/203.15; 261/92; 261/DIG. 65
[58] Field of Search ...................... 128/200.14, 200.17, 128/200.18, 200.21, 203.25, 203.29, 203.15, 203.23; 261/92, DIG. 65; 272/99; 222/630; 239/338; 604/58

[56] References Cited

U.S. PATENT DOCUMENTS

| | | | |
|---|---|---|---|
| 1,202,877 | 10/1916 | Morgan | 128/203.25 |
| 2,674,999 | 4/1954 | Cox | 128/203.25 |
| 3,229,450 | 1/1966 | Stern | 128/200.17 |
| 3,711,071 | 1/1973 | Urbanowicz | 261/92 |
| 4,025,070 | 5/1977 | McGill et al. | 272/99 |
| 4,147,166 | 4/1979 | Hansen | 128/203.15 |

FOREIGN PATENT DOCUMENTS

| | | | |
|---|---|---|---|
| 23371 | 10/1882 | Fed. Rep. of Germany | 128/200.14 |
| 25422 | 4/1883 | Fed. Rep. of Germany | 128/200.14 |
| 534593 | 3/1922 | France | 128/200.14 |
| 549747 | 2/1923 | France | 128/200.14 |
| 458263 | 7/1950 | Italy | 128/203.15 |
| 0003842 | of 1889 | United Kingdom | 604/58 |
| 179142 | 10/1923 | United Kingdom | 128/200.14 |
| 916196 | 1/1963 | United Kingdom | 128/200.17 |

*Primary Examiner*—Henry J. Recla
*Assistant Examiner*—Karin M. Reichle
*Attorney, Agent, or Firm*—Murray Schaffer

[57] ABSTRACT

The apparatus is self-contained for carriage in a pocket or handbag and comprises a nebulizing chamber 12 from which tangentially extends an outlet tube 14 leading to a perpendicular head 15 provided with a mouthpiece 16. The chamber is cylindrical and houses a rotatable disc 25. An adjustable inlet 30 is provided in the chamber and material to be nebulized is introduced to the chamber 12. The disc 25 is driven by a battery and electric motor in the casing 29 and both draws air in through the inlet and breaks up the material in the casing to nebulize it. Baffles 40, 41 control the size of particles expelled and a damping connection 44 reduces unpleasantness to the user from vibrations.

13 Claims, 8 Drawing Figures

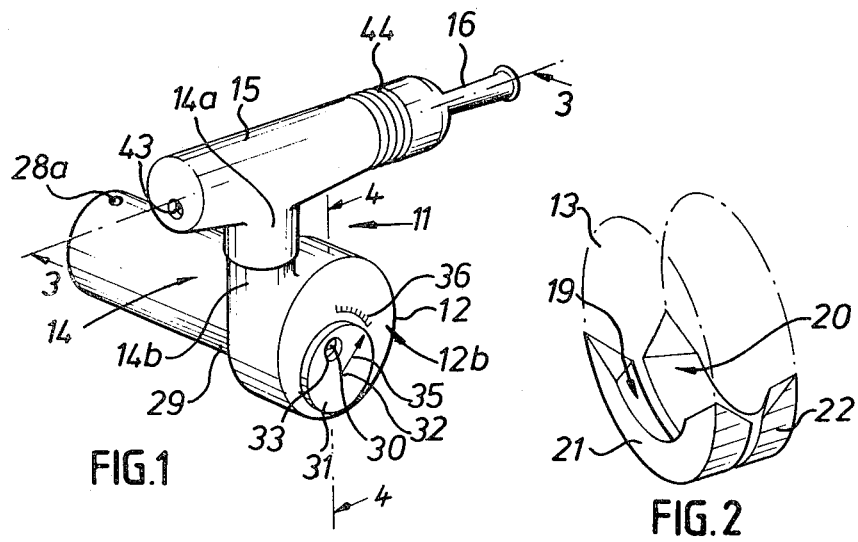
FIG.1
FIG.2
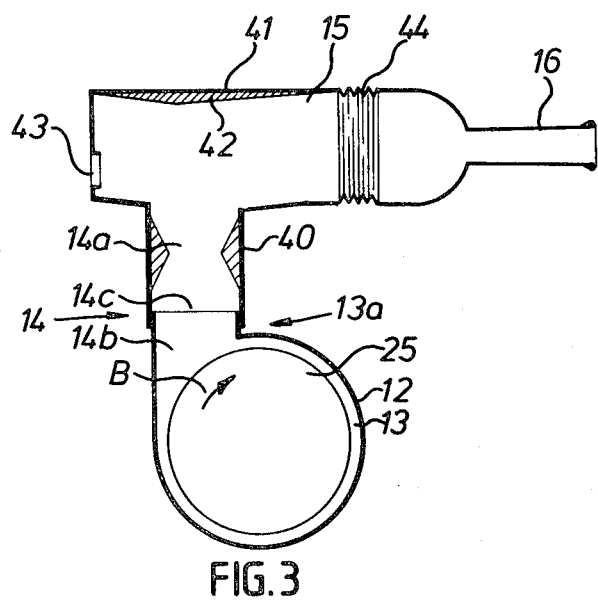
FIG.3

MEDICAL NEBULIZING APPARATUS

BACKGROUND OF THE INVENTION

The present invention relates to medical nebulising apparatus for inhalatory use. In this specification, the term "nebulisation" is intended to include the formation of a spray from a powder as well as from a liquid.

In the medical field, the inhalation of nebulised drugs is an accepted way of treating various medical conditions such as asthma, bronchitis, cystic fibrosis and other conditions of the respiratory tract. Existing medical nebulisers are not easy to use by all patients. They are expensive, bulky and require a separate compressed air or oxygen supply, e.g. from a compressed air container or from an electric compressor device. A patient, therefore, is unlikely to have or carry his own nebuliser and has to visit a hospital for inhalation treatment.

It has been proposed to use a rotatable disc for dispersing particles in a medical nebuliser. The material is fed in an axial direction onto the disc to disperse the particles in a large chamber and an airstream is independently generated to carry particles out of the chamber. There is, therefore, a generation of a large proportion of large particles and the apparatus is massive.

One common way of producing a spray is by the use of a pressurised can, commonly used, for example, for such purposes as paint spraying, air fresheners and insecticide sprays. Although these cans are readily portable and are used as inhalation devices, they suffer several drawbacks. They require a pressurised carrier gas, which itself is undesirable for environmental reasons and the pressure is excessively high, with the result that the spray particles impact in the mouth and coalesce. The devices are not re-usable and they need a very high degree of coordination and effort by the patient.

SUMMARY OF THE INVENTION

The present invention provides medical nebulising apparatus, comprising a housing including a chamber provided with a reservoir for material to be nebulised. The housing has an outlet portion for the nebulised material, a passage for the nebulised material between the chamber and the outlet portion, and nebulising means in the form of a driven rotatable member for effecting nebulisation. The rotatable member has its path of rotation passing through the reservoir to pick up material. The passage communicates with the chamber at a port radially spaced from the path of rotation and positioned in the path of particles flung from the rotatable member. The chamber is shaped to direct particles to the port in an air stream centrifugally generated by the rotatable member.

The rotatable element is preferably in the form of a rotatable disc and the chamber preferably has a circular peripheral wall about the disc periphery. The passage from the chamber may be tangential to the chamber.

The air inlet is preferably an aperture in a wall of the chamber and a shutter may be provided to control the area of the inlet. It is preferred that a scale is provided to indicate the position of the shutter and, therefore, provide predetermined settings for the inlet area. The size of the inlet area determines the rate of delivery of the nebulised material by controlling the rate of admission of air to the chamber during operation.

The passage between the chamber and the outer portion preferably includes a baffle arrangement to assist in controlling the particle size at the outlet by returning larger particles to the chamber.

Apparatus according to the invention can be made sufficiently small for carrying in a pocket or handbag and can provide a fine mist with particles not exceeding $30\mu$ or even particles not exceeding a size as low as $15\mu$.

REVIEW OF PRIOR ART

The use of a rotating wheel for flinging particles into a gas stream is a very old practice in some industries, for example, for comminuting metals and electrostatic powder coating. These industrial processes are described in the following U.K. patent specifications, which have been located by searching, since the invention was made.

U.K. Pat. No. 1,173,380 describes an apparatus for developing electrostatic charge images which involves the use of a disc electrode in an enclosed chamber which dips, while revolving, in a dye liquid. A high voltage is applied to the electrode to cause atomization of the dye liquid and the atomised particles migrate, by virtue of an applied electrical field, to a conductive support for a recording material carrying a charge image.

U.K. Pat. No. 1,085,092 describes an apparatus which uses a rotating toothed-disc to direct liquid particles from a reservoir into a gas stream. This apparatus essentially requires a separate supply of gas under pressure to enable the apparatus to function.

An apparatus for comminuting molten metal for the purpose of, for example, producing an oxide of that metal is described in U.K. Pat. No. 519,784, and a very similar apparatus is described in U.K. Pat. No. 574,385. The apparatus of each of these specifications requires a vessel for containing a mass of molten metal and a rotating wheel flings the particles of the molten metal into a gas stream. Specification No. 519,784, which was published forty years ago, does fleetingly, in one sentence, consider that the rotating wheel might serve to produce the gas stream, but for these industrial processes, as for present day medical nebulisers, it is accepted that a separate gas stream-producing apparatus is essential.

BRIEF DESCRIPTION OF DRAWING

Reference is now made to the accompanying drawings, wherein:

FIG. 1 is a perspective view of a first embodiment of a medical nebulising apparatus according to the invention;

FIG. 2 is a perspective view of a broken away portion of the apparatus of FIG. 1 showing a reservoir thereof;

FIG. 3 is a sectional side elevation on the line 3—3 of FIG. 1;

DESCRIPTION OF THE INVENTION

Figure 4:
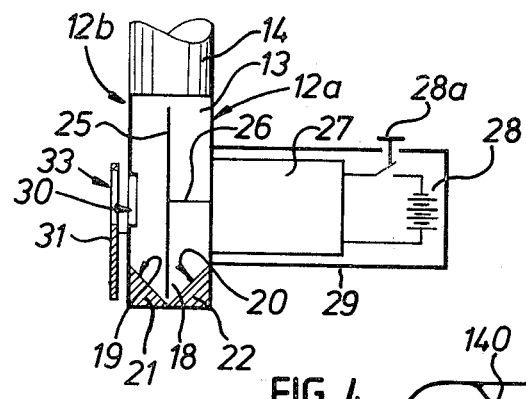
FIG. 4 is a sectional view on the line 4—4 of FIG. 1.
Figure 5:
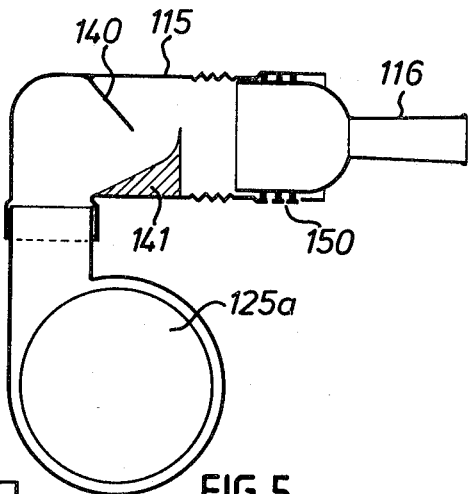
FIGS. 5 and 6 are sectional views similar to FIGS. 3 and 4 of a second embodiment.
Figure 6:
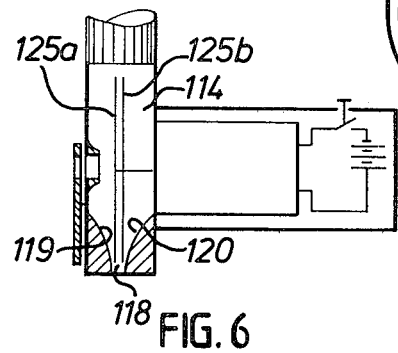
Figure 7:
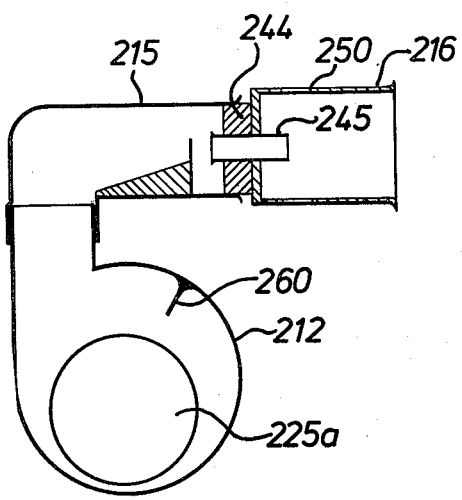
FIGS. 7 and 8 are sectional views similar to FIGS. 3 and 4 of a third embodiment.
Figure 8:
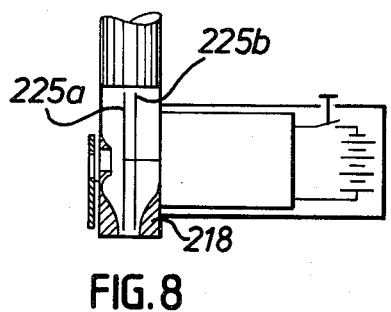

Referring to FIGS. 1 to 4, there is shown a medical nebulising apparatus comprising a housing 11 having a hollow cylindrical portion 12 having a chamber 13 therein. An outlet tube 14 leads upwardly (in the position of use shown in FIG. 1) from the cylindrical portion to define as outlet passage tangential to the chamber 13 and communicating therewith through a port 13a. The outlet tube 14 leads to a tubular head 15, which has a T connection with the tube 14. A mouthpiece 16 is connected to one end of the head 15. In use, material to be nebulised is contained in the chamber 12 and a fine spray consisting of an air stream entraining particles of the material is provided at the mouthpiece, as described hereafter.

The lower portion of the chamber 13 opposite to the tube 14 defines a reservoir 18 and internal sloping surfaces 19, 20 cause the reservoir to narrow towards the periphery, each sloping surface being arcuate and following the internal peripheral contour of the chamber as is apparent from FIG. 2. Each surface is defined in this construction by a solid internal wall 21, 22 of substantially triangular section as is apparent from FIG. 4.

A nebulising disc 25 is rotatably mounted in the chamber 13 by an axle 26, so that part of the marginal periphery of the disc lies between the sloping surfaces 19, 20 in the reservoir, the diameter of the disc being only slightly less than that of the container and the general plane of the disc being parallel to the side walls **12*a*, 12*b* of the cylindrical portion 12. The axle is driven by an electrical motor 27 and a replaceable electric battery 28 mounted in a casing 29 on one side wall 12*a* of the cylindrical portion 12, which defines the chamber 13. A switch 28*a*** is accessible externally of the casing and is actuatable to operate the motor.

The opposite side wall **12*b* of this portion has a central air inlet 30, the size of which is variable by means of a shutter 31. The shutter in this embodiment is in the form of a disc pivotally mounted by pivot pin 32 on the side wall 12*b*. The shutter has an aperture 33 of equal diameter to the inlet 30, so that the inlet is fully open with the aperture 33 and the inlet in register. The shutter can be angularly moved to reduce the area of the inlet exposed. The shutter carries a pointer 35 associated with an arcuate scale 36 marked on the side wall 12*b***, so that a predetermined area of the inlet can be exposed recording the scale reading.

The outlet parts of the device have an internal baffle arrangement defined by a constriction 40 near the mouth of the outlet tube 14, adjacent the head 15, and a conical projection 41 provided in the head 15 directly opposite the outlet tube 14, the apex 42 of the projection 41 being on the axis of the outlet tube. The end of the head opposite to the mouthpiece 16 is closed except for a vent 43. A flexible bellows 44 attaches the mouthpiece 16 to the head 15.

The outlet tube 14 comprises an upper part **14*a*, integral with the head 15 and a lower part 14*b*, integral with the cylindrical portion 12. The upper and lower parts are push-fitted together. The head 15, with the upper part 14*a*, can, therefore, be removed, so that the mouth 14*c*** of the lower part defines an inlet.

In use, the material to be nebulised is introduced to the reservoir 18 through the inlet mouth **14*c*. The patient's mouth is put to the mouthpiece 16 and the electric motor is energised by operating the switch 28*a*. The nebulising disc 25 is thereby rotated in the direction of arrow B in FIG. 3. A part of the periphery is immersed in the material in the reservoir 18, so that the disc flings particles of the material along the tangential passage in the outlet tube 14. The rotating disc also serves as a centrifugal pump to draw air in through the inlet 30 and produce a gas stream along the passage in the outlet tube, the particles of the material being entrained in the gas stream so that nebulised material passes out of the mouthpiece 16 in a fine spray. The amount of air drawn into the chamber can be controlled by the position of the shutter 31**.

As the disc flings particles of the material at a high speed, these particles (especially the larger ones) tend to impact against the inner walls of the chamber 13 and shatter into even smaller particles. The larger particles entering the tube 14 tend to coalesce and drip back into the reservoir 18 or onto the disc for further treatment. This continuous and repeated action leads to the generation of very small particles. The constriction 40 obstructs flow of larger particles and assists the return action to the reservoir as does the conical projection 41 which serves to direct particles which coalesce there back into the reservoir. The spray at the mouthpiece may therefore be made up of particles of maximum size of 15$\mu$.

The vent permits sucking in of extra air by a patient and also prevents a sucking action at the mouthpiece from drawing in material from the reservoir and relieves pressure, if the patient obstructs the mouthpiece or blows back into the mouthpiece. The patient can breathe freely, therefore, without interfering with the operation of the apparatus. Venting in this case also prevents wetting of the material in the reservoir from the user's breath, which is important, if the material is a powder.

The shaping of the reservoir 18 minimises changes in the depth of material therein, with changes in orientation of the apparatus.

The disc may be rotationally mounted off-centre or may be unbalanced about the axis by other means such as weighting to cause vibrations, which assist in breaking up and fluidising the material in the reservoir to improve nebulisation. This may be especially useful where the material is a powder. Large particles incapable of being nebulised in the apparatus could be contained in the reservoir to cause such vibration and assist in breaking the powder particles into even smaller ones.

These vibrations could cause unpleasant sensations in the lips of the user and the flexible bellows 44 serves to damp the vibrations at the mouthpiece.

The disc is preferably rotated at 8000 r.p.m. or more to provide a good rate of delivery of nebulised material.

The described nebulising apparatus is small and is capable of being held in a pocket or handbag. This is assisted by the connection between the tube parts **14*a*, 14*b***, which permits swivelling of the parts to make the apparatus more compact.

The motor casing 29 may be removable to facilitate sterilisation, unless the casing is watertight. The casing may have, for example, a bayonet or screw fitting with the cylindrical portion 12 and the shaft 26 may have two parts with a spline connection. The battery may be recharageable from the mains.

An alternative embodiment is shown in FIGS. 5 and 6, in which the overall construction is substantially the same as the embodiment described above. In this case there are two parallel closely spaced nebulising discs and the internal walls of the reservoir 118 are further spaced at the periphery of the chamber 114 to accommodate the two discs. In this case the walls 119, 120 are convexly curved in section instead of straight.

Instead of the projection 41 and constriction 40, baffles 140, 141 are provided in the head 115. Ventilation holes 150 are optionally provided in this case adjacent to the mouthpiece 116, the size being adjustable by relative movement of the mouthpiece 116 and the rest of the head 115.

FIGS. 7 and 8 show a modification of the embodiment of FIGS. 5 and 6, in which the nebulising discs are eccentrically positioned relative to the peripheral wall of the chamber and are of smaller diameter than in the previously described embodiment. The discs can be rotated in either direction. The discs are positioned near the bottom of the chamber to extend into the reservoir 218, as previously. In this case, a radial baffle 260 is provided in the chamber extending towards the discs. This enhances agitation and disruption of particles within the chamber as a result of impact and also redirects larger particles onto the discs for further treatment.

The mouthpiece 216, in this case is mounted in the outlet from the head 215 by means of a resilient bung 244 to absorb vibrations. An outlet nozzle 245 extends through the bung to communicate the interior of the mouthpiece with the interior of the head. Ventilation holes 250 are provided around the mouthpiece. This arrangement is preferred and is particularly effective to permit the user to breathe freely and to prevent air from the lungs of the user reaching the reservoir.

Each of the described embodiments can be easily cleaned and sterilised.

A very simple arrangement may be effective where the head, such as 15 in FIG. 1, is not provided, but the outlet tube 14 itself may define the mouthpiece. The inlet for air may be defined by the outlet tube, the latter being sufficiently wide to permit sucking of air into the chamber. In this case, a mouthpiece may be provided having an inner outlet tube surrounded by venting, as shown in FIG. 7.

It is envisaged that a nebuliser may be constructed according to the invention for use in an incubator.

The nebuliser may also be usable in non-medical fields, for example, for providing a fine spray in a greenhouse for dispersing an insecticide.

I claim:

1. A portable medical nebulising apparatus capable of being accommodated in a pocket or handbag and comprising a housing defining a chamber having first and second end walls bound by a generally circular peripheral side wall defining a generally circular cross-section, said chamber forming a reservoir for material to be nebulised, air inlet means in one of said end walls of the housing and communicating with the interior of the chamber, a rotatable shaft extending through one of said end walls generally perpendicular to the cross-section of said chamber and extending into said chamber, nebulising means in the form of a disc mounted on said shaft, electrical drive means connected to said shaft to rotate said disc in a path passing at least in part through the reservoir to pick up material in the reservoir and fling particles of the material from the disc, said generally circular peripheral side wall extending around the periphery of the disc, an outlet port in said generally circular peripheral side wall, an outlet passage in communication with said outlet port extending from the peripheral side wall of the chamber outwardly away from the chamber for conveying nebulised particles, a mouthpiece in communication with said outlet passage, the axial dimension of the chamber being narrow relative to the radial dimension, said rotating disc producing an air stream which entrains the nebulised particles picked up by the disc, said air stream being flung outwardly of said outlet port through said outlet passage to said mouthpiece and baffle means provided between said outlet port and said mouthpiece to restrict the passage of particles above a selected predetermined size and to assist the return of larger particles to the chamber, so as to control the size of particles delivered to the mouthpiece by said air stream.

2. Medical nebulising apparatus according to claim 1 wherein the rotatable disc comprises a pair of closely spaced generally parallel discs mounted on said rotatable shaft.

3. Medical nebulising apparatus according to claim 1 wherein the reservoir is defined by a narrowed portion of the chamber opposite to the port.

4. Medical nebulising apparatus according to claim 1 wherein the air inlet means is provided with an adjustable shutter so that the effective area thereof is selectively variable.

5. Medical nebulising apparatus according to claim 4 including means on said housing for indicating the position of said shutter in said inlet opening relative thereto.

6. Medical nebulising apparatus according to claim 1 wherein the rotatable disc is unbalanced to produce vibrations in the reservoir and vibration damping means is provided between the mouthpiece and the housing.

7. Medical nebulising apparatus according to claim 1 wherein the housing includes said outlet passage means defined by a first portion leading from said outlet port and a second portion generally perpendicular to said first portion and leading to said mouthpiece.

8. Medical nebulising apparatus according to claim 7 including one or more vents in said second portion.

9. Medical nebulising apparatus according to claim 7 including one or more vents in said outlet means.

10. Medical nebulizing apparatus according to claim 1 wherein said baffle arrangement is of dimensions sufficient to restrict the passage of particles to a maximum size selected between the range of 15–30μ.

11. Medical nebulizing apparatus according to claim 1 wherein said outlet passage extends tangentially from the peripheral side wall of said chamber.

12. A portable medical nebulising apparatus capable of being accommodated in a pocket or handbag and comprising a housing, defining a chamber having first and second end walls bound by a generally circular peripheral side wall defining a generally circular cross-section therein, said chamber forming a reservoir for material to be nebulised, air inlet means in one of said end walls of the housing and communicating with the interior of the chamber, a rotatable shaft extending through one of said end walls generally perpendicular to the cross-section of said chamber and extending into said chamber, nebulising means in the form of a disc mounted on said rotatable shaft, electrical drive means connected to said shaft to rotate said disk in a path passing at least in part through the reservoir to pick up material in the reservoir and fling particles of the material from the disc, said generally circular peripheral side wall extending around the periphery of the disc, an outlet port in said generally circular peripheral side wall, an outlet passage in communication with said outlet port extending tangentially from the peripheral side wall of the chamber for conveying nebulised particles, a mouthpiece in communication with said outlet passage, the axial dimension of the chamber being narrow relative to the radial dimension, said rotating disc producing an air stream which entrains the nebulised particles picked up by the disc, said air stream being flung outwardly of said outlet port through said outlet passage to said mouthpiece.

13. Medical nebulizing apparatus according to claim 12 including baffle means provided between said outlet port and said mouthpiece to restrict the passage of particles above a selected predetermined size and to assist the return of larger particles to the chamber, so as to control the size of particles delivered to the mouthpiece by said air stream.

* * * * *